(12) United States Patent
Gu et al.

(10) Patent No.: US 6,431,446 B1
(45) Date of Patent: Aug. 13, 2002

(54) PRODUCE RECOGNITION SYSTEM AND METHOD

(75) Inventors: Yeming Gu, Suwanee; Donald A. Collins, Jr., Lawrenceville, both of GA (US)

(73) Assignee: NCR Corporation, Dayton, OH (US)

( * ) Notice: Subject to any disclaimer, the term of this patent is extended or adjusted under 35 U.S.C. 154(b) by 0 days.

(21) Appl. No.: 09/362,487

(22) Filed: Jul. 28, 1999

(51) Int. Cl.[7] ................................................ G06K 7/14
(52) U.S. Cl. ...................................... 235/454; 235/455
(58) Field of Search ............................... 235/454, 455; 356/302, 328

(56) References Cited

U.S. PATENT DOCUMENTS

| | | | |
|---|---|---|---|
| 3,074,634 A | 1/1963 | Gamo ........................ 235/151 |
| 3,737,239 A | 6/1973 | Adams et al. ............... 356/177 |
| 3,796,863 A | 3/1974 | Nickl et al. ........... 235/61.11 E |
| 3,865,490 A | 2/1975 | Grossman .................... 356/76 |
| 3,970,375 A | 7/1976 | Blau, Jr. et al. ............ 350/312 |
| 3,973,849 A | 8/1976 | Jackson et al. ............... 356/97 |
| 4,043,646 A | 8/1977 | Heine et al. ................. 350/315 |
| 4,060,327 A | 11/1977 | Jacobowitz et al. .......... 356/96 |
| 4,106,628 A | 8/1978 | Warkentin et al. ....... 209/74 M |
| 4,120,591 A | 10/1978 | van Valkenburg .......... 356/178 |
| 4,136,954 A | 1/1979 | Jamieson .................... 356/349 |
| 4,175,862 A | 11/1979 | DiMatteo et al. ........... 356/375 |
| 4,260,262 A | 4/1981 | Webster ....................... 356/418 |
| 4,281,933 A | 8/1981 | Houston et al. ............. 356/425 |
| 4,319,830 A | 3/1982 | Roach ........................... 355/1 |
| 4,515,275 A | 5/1985 | Mills et al. .................. 209/558 |
| 4,529,308 A | 7/1985 | Rife ............................ 356/323 |
| 4,532,757 A | 8/1985 | Tutle .......................... 56/328 R |
| 4,534,470 A | 8/1985 | Mills .......................... 209/585 |
| 4,558,786 A | 12/1985 | Lane ........................... 209/558 |
| 4,558,953 A | 12/1985 | Yamada ....................... 356/409 |
| 4,661,985 A | 4/1987 | Akutsu ........................... 382/8 |
| 4,678,904 A | 7/1987 | Saaski et al. ................ 250/227 |
| 4,693,330 A | 9/1987 | Uchimura et al. | |
| 4,693,378 A | 9/1987 | Azegami et al. ............ 209/586 |
| 4,735,323 A | 4/1988 | Okada et al. ................ 209/582 |
| 4,750,161 A | 6/1988 | Takeuchi et al. .............. 369/45 |
| 4,779,982 A | 10/1988 | Koshi et al. ................. 356/318 |
| 4,810,937 A | 3/1989 | Havel .......................... 315/152 |
| 4,888,647 A | 12/1989 | Wada .......................... 358/474 |
| 4,899,348 A | 2/1990 | Kiya et al. ..................... 372/38 |
| 4,907,884 A | 3/1990 | Wyatt et al. ................. 356/336 |
| 4,917,500 A | 4/1990 | Lugos ......................... 356/406 |
| 4,928,008 A | 5/1990 | Huggins et al. .......... 250/231.1 |
| 4,930,865 A | 6/1990 | Dosmann ..................... 350/169 |
| 4,944,594 A | 7/1990 | Burk ........................... 356/446 |
| 4,954,972 A | 9/1990 | Sullivan ...................... 364/526 |
| 4,964,053 A | 10/1990 | Humble ....................... 364/466 |
| 4,968,138 A | 11/1990 | Scott et al. .................. 356/121 |
| 5,000,569 A | 3/1991 | Nylund ........................ 356/237 |
| 5,021,645 A | 6/1991 | Satula et al. ............ 250/223 R |
| 5,060,290 A | 10/1991 | Kelly et al. .................... 382/18 |

(List continued on next page.)

FOREIGN PATENT DOCUMENTS

| | | |
|---|---|---|
| EP | 0692703 | 1/1996 |
| EP | 0758081 | 12/1997 |
| JP | 2000-155767 | * 6/2000 |
| WO | 9746856 | 12/1997 |
| WO | 9839627 | 9/1998 |

Primary Examiner—Karl D. Frech
(74) Attorney, Agent, or Firm—Paul W. Martin

(57) ABSTRACT

A produce recognition system and method which use an internal reference to calibrate a produce data collector. The produce data collector collects first data from an external reference, collects second and third data from an internal reference, and collects fourth data from a produce item. A computer determines a first calibration value from the first and second data and a second calibration value from the third data and applies the first and second calibration values to the fourth data to produce fifth data. The computer further obtains sixth data from reference produce data and compares the fifth and sixth data to identify the produce item.

10 Claims, 6 Drawing Sheets

U.S. PATENT DOCUMENTS

| | | | |
|---|---|---|---|
| 5,083,638 A | 1/1992 | Schneider | 186/61 |
| 5,085,325 A | 2/1992 | Jones et al. | 209/580 |
| 5,095,319 A | 3/1992 | Watarai et al. | 346/108 |
| 5,097,291 A | 3/1992 | Suzuki | 355/69 |
| 5,115,888 A | 5/1992 | Schneider | 186/61 |
| 5,153,926 A | 10/1992 | Jansson et al. | 382/54 |
| 5,247,373 A | 9/1993 | Iwama et al. | 358/471 |
| 5,253,765 A | 10/1993 | Moorehead et al. | 209/539 |
| 5,286,980 A | 2/1994 | Richert | 250/560 |
| 5,309,270 A | 5/1994 | Yamakawa | 359/196 |
| 5,319,437 A | 6/1994 | Van Aken et al. | 356/326 |
| 5,325,445 A | 6/1994 | Herbert | 382/38 |
| 5,333,739 A | 8/1994 | Stelte | 209/582 |
| 5,335,293 A | 8/1994 | Vannelli et al. | 382/17 |
| 5,339,107 A | 8/1994 | Henry et al. | 348/270 |
| 5,375,177 A | 12/1994 | Vaidyanathan et al. | 382/48 |
| 5,416,577 A | 5/1995 | Haggerty et al. | 356/300 |
| 5,420,681 A | 5/1995 | Woodruff | 356/326 |
| 5,426,282 A | 6/1995 | Humble | 235/383 |
| 5,428,558 A | 6/1995 | Cahill et al. | 364/571.02 |
| 5,444,528 A | 8/1995 | Puschell | 356/73 |
| 5,449,911 A | 9/1995 | Creeze | 250/341.7 |
| 5,453,883 A | 9/1995 | Chazallet | 359/890 |
| 5,461,698 A | 10/1995 | Schwanke et al. | 395/22 |
| 5,471,052 A | 11/1995 | Ryczek | 250/226 |
| 5,471,311 A | 11/1995 | van den Bergh et al. | 356/446 |
| 5,479,258 A | 12/1995 | Hinnrichs et al. | 356/326 |
| 5,483,335 A | 1/1996 | Tobias | 356/310 |
| 5,483,339 A | 1/1996 | Van Aken et al. | 356/326 |
| 5,494,136 A | 2/1996 | Humble | 186/61 |
| 5,495,096 A | 2/1996 | Ogata et al. | 235/462 |
| 5,497,314 A | 3/1996 | Novak | 364/403 |
| 5,537,488 A | 7/1996 | Menon et al. | 382/170 |
| 5,546,475 A | 8/1996 | Bolle et al. | 382/190 |
| 5,642,197 A | 6/1997 | Tuhro et al. | 356/418 |
| 5,646,399 A | 7/1997 | Fukushima et al. | 250/226 |
| 5,649,070 A | 7/1997 | Connell et al. | 395/77 |
| 5,659,624 A | 8/1997 | Fazzari et al. | 382/110 |
| 5,675,070 A | 10/1997 | Gelperin | 73/23.34 |
| 5,675,419 A | 10/1997 | Van Den Bergh et al. | 356/446 |
| 5,678,132 A | 10/1997 | Shiba et al. | 399/59 |
| 5,680,220 A | 10/1997 | Delignieres et al. | 356/406 |
| 5,684,582 A | 11/1997 | Eastman et al. | 356/328 |
| 5,703,960 A | 12/1997 | Soest | |
| D389,076 S | 1/1998 | Beckstrom et al. | D10/91 |
| 5,867,265 A * | 2/1999 | Thomas | 356/328 |

* cited by examiner

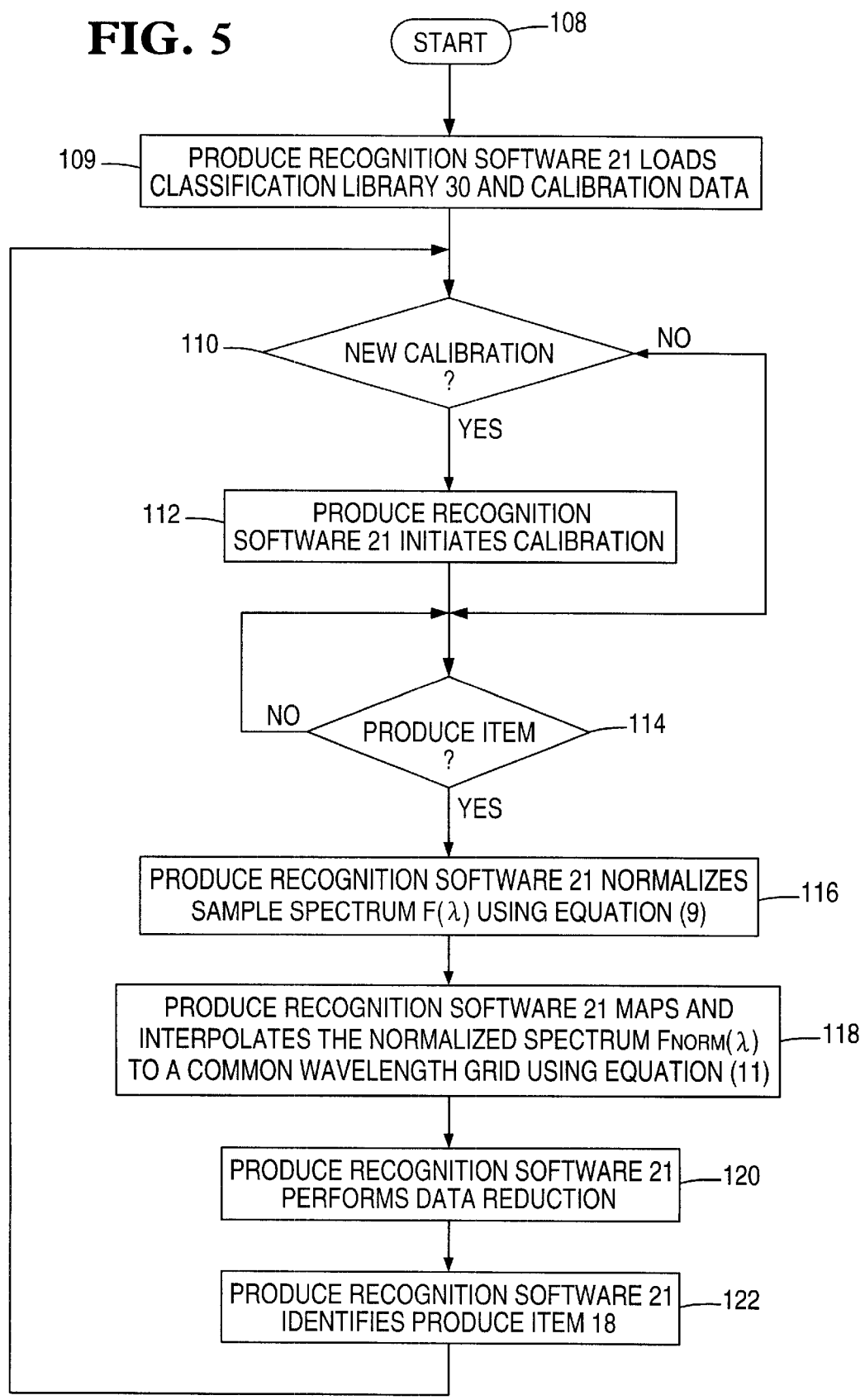

PRODUCE RECOGNITION SYSTEM AND METHOD

CROSS-REFERENCE TO RELATED APPLICATIONS

The present invention is related to the following commonly assigned and co-pending U.S. application:

"Produce Data Collector And Produce Recognition System", filed Nov. 10, 1998, invented by Gu et al., and having a Ser. No. 09/189,783.

BACKGROUND OF THE INVENTION

The present invention relates to product checkout devices and more specifically to a produce recognition system and method.

Bar code readers are well known for their usefulness in retail checkout and inventory control. Bar code readers are capable of identifying and recording most items during a typical transaction since most items are labeled with bar codes.

Items which are typically not identified and recorded by a bar code reader are produce items, since produce items are typically not labeled with bar codes. Bar code readers may include a scale for weighing produce items to assist in determining the price of such items. But identification of produce items is still a task for the checkout operator, who must identify a produce item and then manually enter an item identification code. Operator identification methods are slow and inefficient because they typically involve a visual comparison of a produce item with pictures of produce items, or a lookup of text in table. Operator identification methods are also prone to error, on the order of fifteen percent.

Therefore, it would be desirable to provide a produce recognition system and method. It would also be desirable to provide a produce data collector with a reference apparatus that makes calibration easier.

SUMMARY OF THE INVENTION

In accordance with the teachings of the present invention, a produce recognition system and method are provided.

The produce recognition system includes a produce data collector and a computer. The produce data collector collects first data from an external reference, collects second and third data from an internal reference, and collects fourth data from a produce item. A computer determines a first calibration value from the first and second data and a second calibration value from the third data and applies the first and second calibration values to the fourth data to produce fifth data. The computer further obtains sixth data from reference produce data and compares the fifth and sixth data to identify the produce item.

A method of identifying a produce item includes the steps of obtaining calibration information for a produce data collector, collecting first data describing the produce item by the produce data collector, applying the calibration information to the first data to produce second data, obtaining a number of previously stored third data associated with a plurality of produce items, comparing the second data to the third data to determine fourth data and a corresponding produce item from the third data which is most like the second data, and identifying the produce item to be the corresponding produce item.

A method of calibrating produce data collected by a produce data collector includes the steps of obtaining a first calibration value for the produce data collector using an external reference and an internal reference, obtaining a second calibration value for the produce data collector using only the internal reference, and applying the first and second calibration values to the produce data.

It is accordingly an object of the present invention to provide a produce recognition system and method.

It is another object of the present invention to provide a produce recognition system and method which identifies produce items by comparing their spectral data with those in a spectral data library.

It is another object of the present invention to provide the produce data collector with a reference apparatus that makes calibration easier.

It is another object of the present invention to provide the produce data collector with an internal reference for automatic calibration.

It is another object of the present invention to provide a produce data collector which uses an internal reference for indirect inter-device calibration.

It is another object of the present invention to provide an indirect inter-device calibration method for a produce data collector.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

FIG. 5 is a flow diagram illustrating a produce recognition method of the present invention.

DETAILED DESCRIPTION OF THE PREFERRED EMBODIMENT

Figure 1:
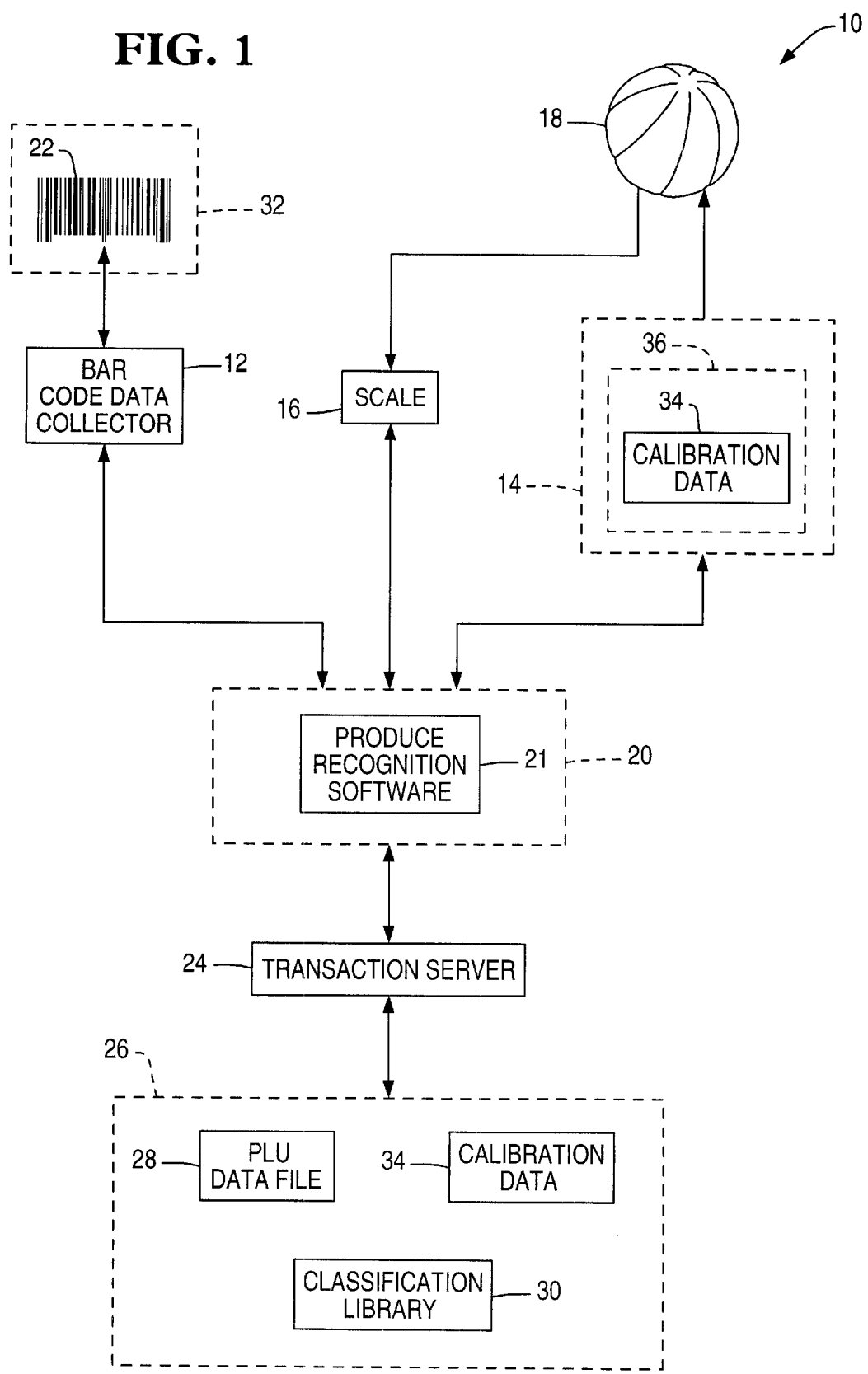
FIG. 1 is a block diagram of a transaction processing system including a produce recognition system.

Referring now to FIG. 1, transaction processing system 10 includes bar code data collector 12, produce data collector 14, and scale 16.

Bar code data collector 12 reads bar code 22 on merchandise item 32 to obtain an item identification number, also know as a price look-up (PLU) number, associated with item 32. Bar code data collector 12 may be any bar code data collector, including an optical bar code scanner which uses laser beams to read bar codes. Bar code data collector 12 may be located within a checkout counter or mounted on top of a checkout counter.

Produce data collector 14 collects data for produce item 18 or any other non-barcoded merchandise item. Such data preferably includes color or spectral data, but may also include size data, shape data, surface texture data, and aromatic data.

Produce data collector 14 includes memory 36 for storing device-specific calibration data 34. Memory 36 may include a flash read-only-memory (ROM).

Classification library 30 is a data library derived from previously collected and processed produce data. It contains information about different produce items, or types of produce items called classes, each of which is associated with a PLU number.

During a transaction, operation of produce data collector 14 may be initiated by placement of produce item 18 on the data collector window 60 (FIG. 2) or by operator-initiated commands from transaction terminal 20. Window 60 is integrated into the cover plate of scale 16, such that produce item 18 is weighed by scale 16 and viewed by produce data collector 14 at the same time.

Scale 16 determines a weight for produce item 18. Scale 16 works in connection with bar code data collector 12, but may be designed to operate and be mounted separately. Scale 16 sends weight information for produce item 18 to transaction terminal 20 so that transaction terminal 20 can determine a price for produce item 18 based upon the weight information.

Bar code data collector 12 and produce data collector 14 operate separately from each other, but may be integrated together. Bar code data collector 12 works in conjunction with transaction terminal 20 and transaction server 24.

In the case of bar coded items, transaction terminal 20 obtains the item identification number from bar code data collector 12 and retrieves a corresponding price from PLU data file 28 through transaction server 24.

In the case of non-bar coded produce items, transaction terminal 20 executes produce recognition software 21 which obtains produce characteristics from produce data collector 14, identifies produce item 18 by comparing the collected produce data with classification library 30, retrieves a corresponding price from PLU data file 28.

Produce recognition software 21 manages calibration of produce data collector 14 and maintains calibration data 34. Calibration data 34 includes device-specific calibration data on each produce data collector 14 in system 10.

In an alternative embodiment, identification of produce item 18 may be handled by transaction server 24. Transaction server 24 receives collected produce characteristics and identifies produce item 18 using classification library 30. Following identification, transaction server 24 obtains a price for produce item 18 and forwards it to transaction terminal 20.

Storage medium 26 preferably includes one or more hard disk drives. PLU data file 28, classification library 30, and calibration data 34 are stored within storage medium 26, but each may also be located instead at transaction terminal 20. PLU data file 28 may be located in bar code data collector 12. Calibration data 34 may also be stored within individual produce data collectors 14.

To assist in proper identification of produce items, produce recognition software 21 may additionally display candidate produce items for operator verification. Produce recognition software 21 preferably arranges the candidate produce items in terms of probability of match and displays them as text and/or color images on an operator display of transaction terminal 20. The operator may accept the most likely candidate returned by or override it with a different choice.

Figure 2:
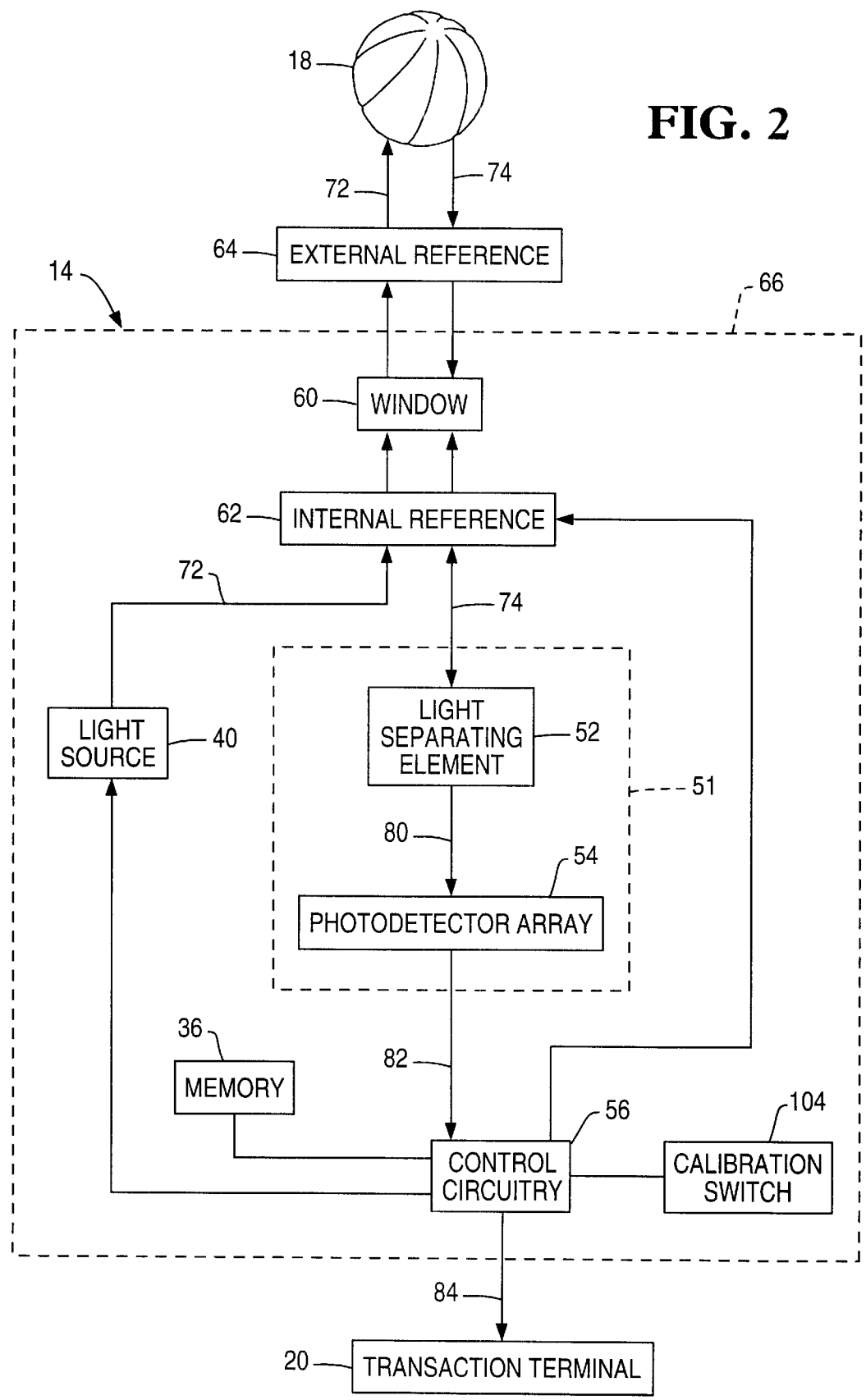
FIG. 2 is a block diagram of a type of produce data collector which collects spectral data.
Figure 3:
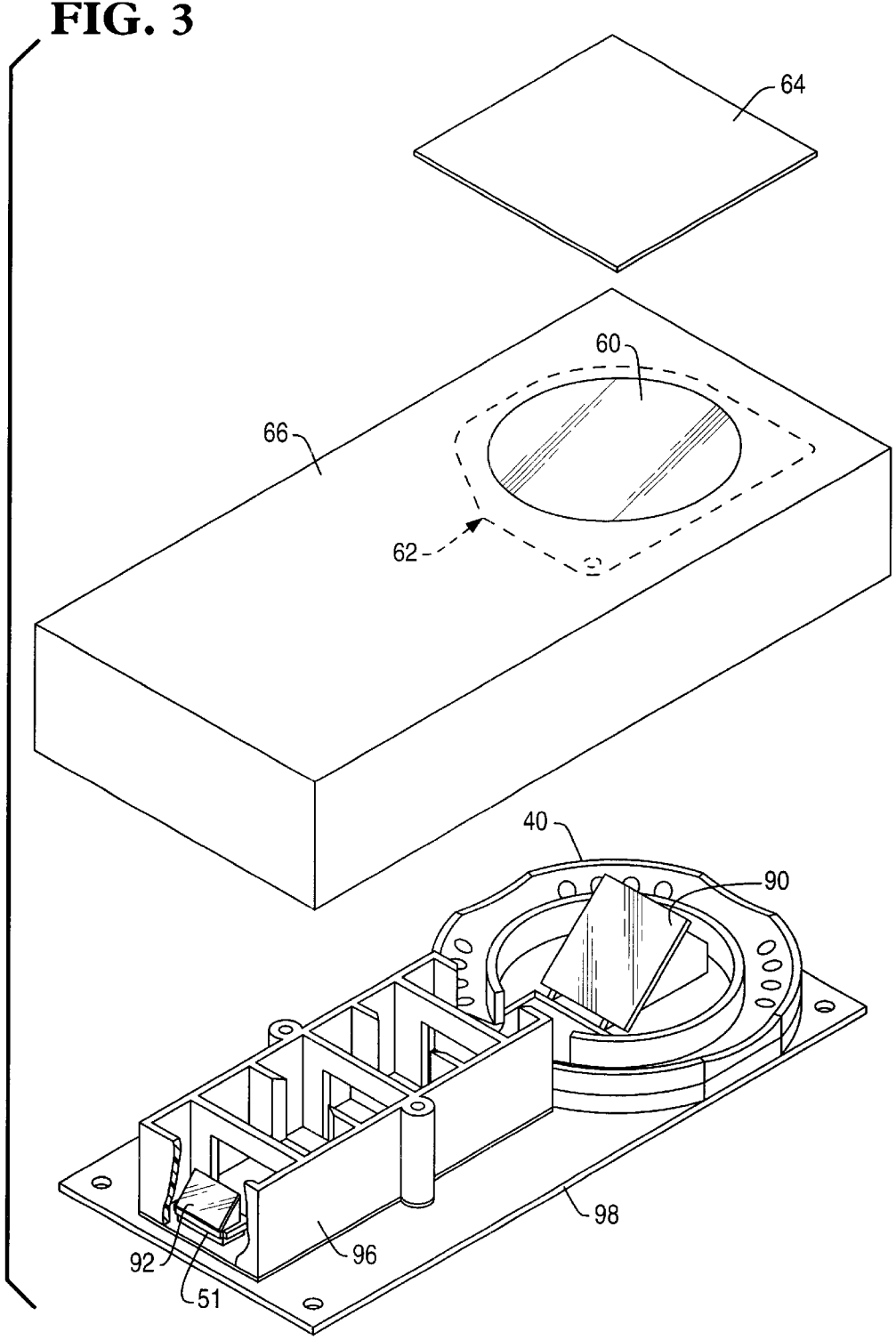
FIG. 3 is a perspective view of the produce data collector illustrating placement of external and internal references.

Turning now to FIGS. 2 and 3, produce data collector 14 primarily includes light source 40, spectrometer 51, control circuitry 56, transparent window 60, internal reference 62, and housing 66.

Light source 40 produces light 70. Light source 40 preferably produces a white light spectral distribution, and preferably has a range from 400 nm to 700 nm, which corresponds to the visible wavelength region of light.

Light source 40 preferably includes one or more light emitting diodes (LED's). A broad-spectrum white light producing LED, such as the one manufactured by Nichia Chemical Industries, Ltd., is preferably employed because of its long life, low power consumption, fast turn-on time, low operating temperature, good directivity. Alternate embodiments include additional LED's having different colors in narrower wavelength ranges and which are preferably used in combination with the broad-spectrum white light LED to even out variations in the spectral distribution and supplement the spectrum of the broad-spectrum white light LED.

Other types of light sources 40 are also envisioned by the present invention, although they may be less advantageous than the broad spectrum white LED. For example, a tungsten-halogen light may be used because of its broad spectrum, but produces more heat.

A plurality of different-colored LEDs having different non-overlapping wavelength ranges may be employed, but may provide less than desirable collector performance if gaps exist in the overall spectral distribution.

Spectrometer 51 includes light separating element 52, photodetector array 54.

Light separating element 52 splits light 76 in the preferred embodiment into light 80 of a continuous band of wavelengths. Light separating element 52 is preferably a linear variable filter (LVF), such as the one manufactured by Optical Coating Laboratory, Inc., or may be any other functionally equivalent component, such as a prism or a grating.

Photodetector array 54 produces spectral signals 82. The pixels of the array spatially sample the continuous band of wavelengths produced by light separating element 52, and produce a set of discrete signals. Photodetector array 54 is preferably a complimentary metal oxide semiconductor (CMOS) array, but could be a Charge Coupled Device (CCD) array.

Control circuitry 56 controls operation of produce data collector 14 and produces digitized spectral signals 84. The digitized spectrum represent a series of data points for narrow wavelength bands. These data points make up the measured spectrum $F(\lambda)$ of produce item 18, where $\lambda$ is the center wavelength of various wavelength bands. For this purpose, control circuitry 56 includes an on-board digital controller/processor, which contains multiple analog-to-digital (A/D) and digital-to-analog (D/A) converters. For a detector array with 1000:1 signal-to-noise ratio, a 12-bit A/D converter with a sampling rate of 22–44 kHz produces acceptable results.

Transparent window 60 includes an anti-reflective surface coating to prevent light 72 reflected from window 60 from contaminating reflected light 74.

Internal reference 62 is used for purposes of indirectly calibrating produce data collector 14. External reference 64 is used for direct calibration. Both internal and external references are made of materials which are diffusely reflective, and are white or gray in color. The material and its color should be stable in time and against changes in environmental conditions. Commercially available ceramic references may be used as external references. Internal reference materials should be light in weight and easy to work with. Certain types of white or gray plastic material (e.g., ABS polycarbon) are suitable for use as internal references.

Calibration data 34 includes correction function $C_{dev}(\lambda)$ and the measured spectrum $F'_{ref}(\lambda)$ of internal reference 62. Correction function $C_{dev}(\lambda)$ is determined during manufacture or field installation of produce data collector 14 using measured spectrum $F'_{ref}(\lambda)$ of internal reference 62 and measure spectrum $F_{ref}(\lambda)$ of external reference 64. Internal measured spectrum $F'_{ref}(\lambda)$ is also determined subsequently during an internal calibration procedure. Calibration data 34 may also include mapping and/or interpolation data specific to each produce data collector 14.

Housing 66 contains light source 40, spectrometer 51, photodetector array 54, control circuitry 56, transparent window 60, and internal reference 62.

In operation, an operator places produce item 18 on window 60. Control circuitry 56 turns on light source 40. Light separating element 52 separates reflected light 74 into different wavelengths to produce light 80 of a continuous band of wavelengths. Photodetector array 54 produces spectral signals 82 containing produce data. Control circuitry 56 produces digitized produce data signals 84 which it sends to transaction terminal 20. Control circuitry 56 turns off light source 40 and goes into a wait state.

Transaction terminal 20 uses produce data in digitized produce data signals 84 to identify produce item 18. Here, produce data consists of digitized spectra which transaction terminal 20 processes and identifies using information provided in classification library 30. After identification, transaction terminal 20 obtains a unit price from PLU data file 28 and a weight from scale 16 in order to calculate a total cost of produce item 18. Transaction terminal 20 enters the total cost into the transaction.

From time to time, produce data collector 14 must be calibrated. Preferably, produce recognition software 21 controls operation of internal reference 62 in order to minimize operator involvement. Calibration may be conducted during each produce transaction or based upon a predetermined schedule. However, switch 104 may be used by an employee or technician to signal control circuitry 56 to initiate calibration.

Normally, a common external reference 64 or references identical to each other in terms of their reflective properties are needed for inter-device calibration.

For ideal linear devices, the measured spectra $F(\lambda)$ for any external object (a produce item or external reference 64) may be expressed as $$F(\lambda)=T(\lambda)S(\lambda)R(\lambda); \tag{1}$$

where $T(\lambda)$ is the system transfer function, $S(\lambda)$ is the source illumination function at window 60, and $R(\lambda)$ is the average diffuse reflection coefficient of the external object.

If the object is external reference 64, the measured spectrum $F_{ref}(\lambda)$ has the same form:

$$F_{ref}(\lambda)=T(\lambda)S(\lambda)R_{ref}(\lambda); \tag{2}$$

where $R_{ref}(\lambda)$ is the average diffuse reflection coefficient of external reference 64. Therefore when the sampled spectrum of an external object is normalized by the external reference spectrum $F_{ref}(\lambda)$, a device-independent measurement of spectral data results:

$$F_{NORM}(\lambda) \equiv \frac{F(\lambda)}{F_{ref}(\lambda)} = \frac{R(\lambda)}{R_{ref}(\lambda)}. \tag{3}$$

Obviously, if the same external reference 64 or identical references are used, the normalized spectra for different produce data collectors 14 will be identical: since there is no device-dependent factors, i.e., $T(\lambda)$ and $S(\lambda)$, on the right-hand side of Equation (3).

For most practical devices, frequent calibration is required, since both the transfer function $T(\lambda)$ and source function $S(\lambda)$ of produce data collector 14 may vary with time and the environment. An external reference measurement using external reference 64 requires operator involvement and can be inconvenient to checkout operations. Internal reference 62 is preferred because it improves operability and reliability by minimizing operator involvement. However, since both the source illumination function $S(\lambda)$ and the system transfer function $T(\lambda)$ are different for internal reference 62 than for the external reference 64, internal reference 62 cannot be used for direct inter-device calibration. Internal reference 62 can be used for indirect inter-device calibration, but only under special conditions.

Indirect calibration is preformed by first calibrating internal reference 62. The measured spectrum $F'_{ref}(\lambda)$ of internal reference 62 is $$F'_{ref}(\lambda)=T'(\lambda) \times S'(\lambda) \times R'_{ref}(\lambda). \tag{4}$$

An initial calibration of internal reference 62 determines $$\frac{F_{ref}(\lambda)}{F'_{ref}(\lambda)} = \frac{T(\lambda)}{T'(\lambda)} \times \frac{S(\lambda)}{S'(\lambda)} \times \frac{R_{ref}(\lambda)}{R'_{ref}(\lambda)}. \tag{5}$$

As mentioned above, special conditions must be met in order to use internal reference 62 for indirect inter-device calibration. One condition is that internal reference 62 must be located and oriented so that its system transfer function $T'(\lambda)$ only differs by a constant factor t from the system transfer function $T(\lambda)$ of external reference 64.

$$\frac{T(\lambda)}{T'(\lambda)} = t(\lambda); \tag{6}$$

where $t(\lambda)$ is in general a function of wavelength $\lambda$ but independent of any system characteristics that may vary with time or environmental conditions. For a spectrometer 51 using a linear variable filter for light separating element 52 combined with a linear diode array detector for photodetector array 54, one way of achieving a constant factor $t(\lambda)$ is by placing internal reference 62 in the direct light path between window 60 and light separating element 52. The only difference between $T(\lambda)$ and $T'(\lambda)$ is now due to the transmission of window 60 and the geometric factors. These differences are, or can be made, very stable factors.

Another condition which must be met in order to use internal reference 62 for indirect inter-device calibration is that the source illumination function $S'(\lambda)$ of internal reference 62 only differs by a factor s from the source illumination function $S(\lambda)$ of external reference 64:

$$\frac{S(\lambda)}{S'(\lambda)} = s(\lambda); \tag{7}$$

where $s(\lambda)$ represents the difference due to geometric parameters, which can be made stable against time and environmental changes.

A final condition which must be met in order to use internal reference 62 for indirect inter-device calibration is that the diffuse-reflection coefficient $R(\lambda)$ of internal reference 62 is stable in time. This is achieved by proper selection of reference material.

In general, the equation for indirect inter-device calibration is:

$$F'_{NORM}(\lambda) \equiv \frac{F(\lambda)}{F'_{ref}(\lambda)} = \frac{F_{ref}(\lambda)}{F'_{ref}(\lambda)} \times \frac{F(\lambda)}{F_{ref}(\lambda)} = C_{dev}(\lambda) \times F_{NORM}(\lambda). \quad (8)$$

Thus, the device-independent spectral measurement as defined in Equation (3) can be obtained through an internal reference by $$F_{NORM}(\lambda) = \frac{1}{C_{dev}(\lambda)} \times F'_{NORM}(\lambda) = \frac{F(\lambda)}{C_{dev}(\lambda) \times F'_{ref}(\lambda)}; \quad (9)$$

where correction function $C_{dev}(\lambda)$ equals:

$$C_{dev}(\lambda) = \frac{F_{ref}(\lambda)}{F'_{ref}(\lambda)} = t(\lambda) \times s(\lambda) \times \frac{R_{ref}(\lambda)}{R'_{ref}(\lambda)}. \quad (10)$$

External reference 64 is only needed for initial calibration to determine the correction function $C_{dev}(\lambda)$. This initial calibration may be during manufacture or field installation of produce data collector 14.

In equations (1) through (10), all measurements and factors are expressed as functions of wavelength $\lambda$. In reality, however, measurements obtained as raw data are functions of pixel positions. To transform these functions of pixels to functions of wavelength, produce data collector 14 needs to be wavelength-calibrated at manufacture. For the spectrometer 51 described in this invention which uses an LVF, the relationship between wavelength and pixel position is linear, and the wavelength-calibration can be easily obtained from a measured spectrum of a line source, such as a mercury-argon (HgAr) lamp.

Let x=1,2, . . . , N be the pixel positions, where N is the total number of pixels, the linear relation between x and wavelength $\lambda$ can be expressed as $$\lambda = C_0 + C_1 \times x; \quad (11)$$

where $C_0$ and $C_1$ are two constant factors. By determining the center-positions of two or more spectral lines in the wavelength range of the linear-variable-filter, the linear mapping parameters $C_0$ and $C_1$ can be computed.

If an LVF and a linear diode array, as taught in example spectrometer 51 above, are permanently fixed together at manufacture, the wavelength mapping will be fixed too. Therefore, wavelength mapping parameters $C_0$ and $C_1$, along with correction function $C_{dev}(\lambda)$, can be determined at manufacture and permanently stored on the produce data collector board, e.g., into memory 36 of the controller/processor chip along with calibration values $C_{dev}(\lambda)$ and $F'_{ref}(\lambda)$. Produce recognition software 21 loads, wavelength mapping parameters $C_0$ and $C_1$ during startup and/or as necessary.

While one type of spectrometer and corresponding mapping function have been disclosed, the present invention anticipates that other types of spectrometers and mapping functions may be employed in a similar fashion.

Equation (11) defines a one-to-one relationship between the pixel position and a device-dependent wavelength grid. By interpolating the normalized spectrum from this grid onto a common wavelength grid, say, from 400 nm to 700 nm with 5 nm intervals, makes the resulting data truly device independent.

With reference to FIG. 3, produce data collector 14 is shown in further detail.

Light source 40 preferably includes a number of white LED's which are specially arranged so that the illumination is uniform in both luminosity and spectrum over the entire surface of window 60 for illuminating produce item 18.

Housing 66 contains window 60 and internal reference 62. External reference 64 is shown above window 64. External reference may be a separate element or mounted to the top surface of housing 66 and activated in a manner similar to internal reference 62.

Turning mirrors 90 and 92 direct reflected light 74 to spectrometer 51.

Light baffle 96 minimizes contamination of reflected light 74 by light 72 from light source 40.

Printed circuit board 98 contains control circuitry 56 and forms a base for mounting light source 40, spectrometer 51, turning mirror 90, turning mirror 92, and light baffle 96. Printed circuit board 98 fastens to housing 66.

Figure 4A:
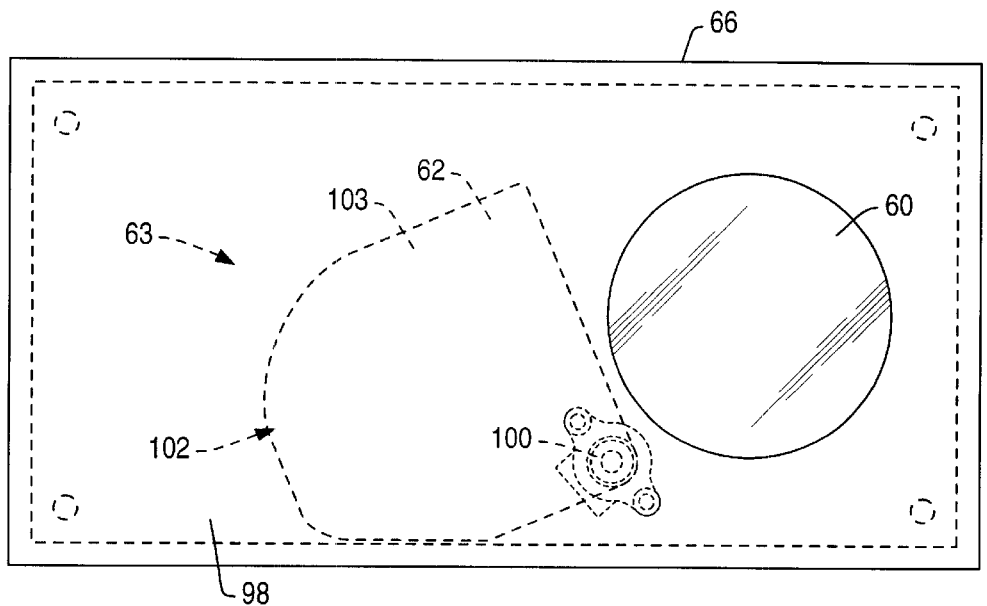
FIGS. 4A and 4B are top and bottom views of a housing of the produce data collector illustrating a placement and operation of the internal reference.
Figure 4B:
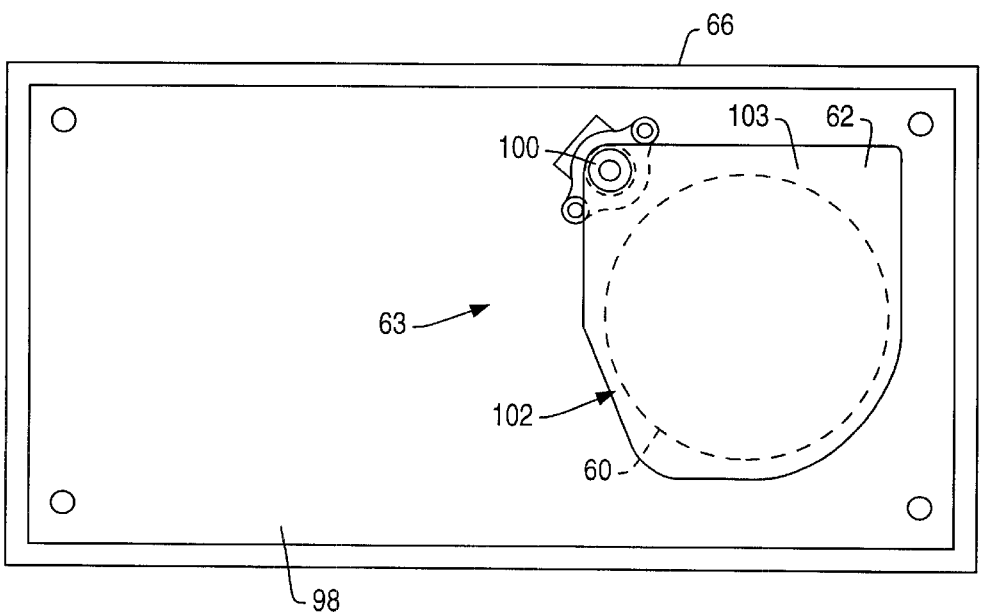

Turning now to FIGS. 4A and 4B, internal reference 62 is shown in further detail. Internal reference 62 is mounted below and adjacent window 60. FIG. 4A shows both housing 66 and printed circuit board 98, while FIG. 4B shows only printed circuit 98.

Internal reference assembly 63 includes motor 100 and shutter 102. Motor 100 is mounted to printed circuit board 90. Shutter 102 is mounted to the shaft of motor 100. Internal reference 62 is either formed as part of shutter 102 or attached to inner surface 103 of shutter 102.

Control circuitry 56 energizes motor 100 to place shutter 102 in an open position (FIG. 4A) and a closed position (FIG. 4B). Calibration readings are taking while shutter 102 is closed. Control circuitry 56 responds to commands from produce recognition software 21 in the automatic mode of operation and from switch 104 in the manual mode of operation.

Turning now to FIG. 5, the produce recognition method of the present invention begins with START 108.

In step 109, produce recognition software 21 loads classification library 30 and calibration data 34. Classification library 30 may be loaded from storage medium 26 through transaction server 24 or from transaction terminal 20.

Calibration data 34 may be loaded from storage medium 26, transaction terminal 20, and/or memory 36. Values $C_0$, $C_1$, $C_{dev}(\lambda)$ are preferably loaded from memory 36. If a previously measured internal reference spectrum $F'_{ref}(\lambda)$ is available for the same produce data collector 14, it may be loaded as initial calibration data until a new calibration is performed.

In step 110, produce recognition software 21 determines whether a new calibration is necessary. During normal operations, produce recognition 21 software and/or produce data collector 14 constantly monitors system performance and stability and automatically determines if a new calibration is needed. Upon system startup, if there is no previously measured internal reference data $F'_{ref}(\lambda)$ available, then a new calibration is required. Produce recognition software 21 may periodically initiate calibration based upon a preset schedule. Alternatively, an operator may force a calibration by issuing a command through transaction terminal 20 or by using switch 104. If a new calibration is necessary, operation proceeds to step 112. If not, operation proceeds to step 113.

Figure 6:
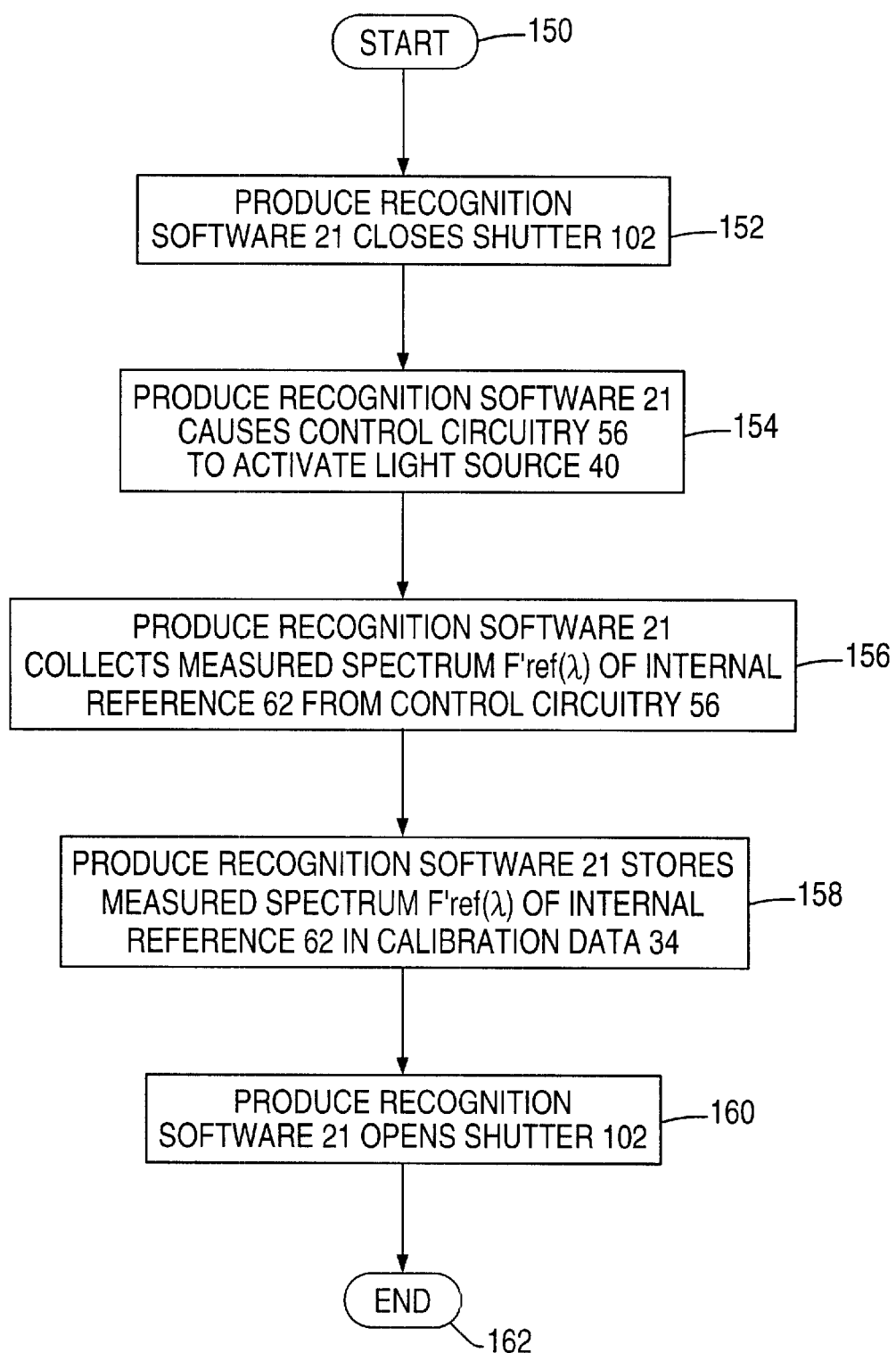
FIG. 6 is a flow diagram illustrating a method of obtaining an internal reference calibration value.

In step 112, produce recognition software 21 initiates calibration to obtain more recent internal reference spectrum $F'_{ref}(\lambda)$ (FIG. 6). Following calibration, operation proceeds to step 114.

In step 114, produce recognition software 21 waits for a signal from produce data collector 14 to identity produce item 18. Preferably, produce data collector 14 is selfactivated. Control circuitry 56 continuously monitors the ambient illumination at window 60 to determine if produce item 18 is placed on window 60. Alternatively, if produce data collector 14 is integrated with scale 16, scale 16 may signal control circuitry 56 when there is a stable weight reading. As another alternative, an operator may manually signal control circuitry 56 to begin data collection through an input device (e.g., keyboard) of transaction terminal 20.

In detail, produce data collector 14 illuminates produce item 18, splits light collected from produce item 18 into a plurality of different light portions in different wavelength bands, converts energy in the plurality of light portions into a plurality of electrical signals, and digitizes the plurality of electrical signals to produce sample spectrum $F(\lambda)$.

If a signal is received from produce data collector 14 by produce recognition software 21, operation proceeds to step 116.

In step 116, produce recognition software 21 normalizes sample spectrum $F(\lambda)$ by dividing it by the product of internal reference spectrum $F'_{ref}(\lambda)$ and the correction function $C_{dev}(\lambda)$ according to equation (9). As mentioned above, internal reference spectrum $F'_{ref}(\lambda)$ and correction function $C_{dev}(\lambda)$ are obtained from memory 36. Internal reference spectrum $F'_{ref}(\lambda)$ may be one which was recently obtained in step 112.

In step 118, produce recognition software 21 maps and interpolates normalized spectrum $F_{NORM}(\lambda)$ onto a fixed wavelength grid, for example, a grid in the visible range from 400 to 700 nm, with 5 nm intervals. For an LVF, equation (11) and a standard linear interpolation method are used for this data reduction step.

In step 120, produce recognition software 21 performs further data reduction that may be required to optimize the identification result. For example, by linearly transforming the spectral data into a lower dimensional space in which the distinguishing features between different classes within library 30 are weighted according to their importance, and the less and non-distinguishing features are disregarded.

In step 122, produce recognition software 21 compares the processed sample data against library 30 and classifies the unknown produce item 18.

The data reduction detail in step 120 and the data format in classification library 30 are all related to the classification process of step 122. One simple classification algorithm uses the nearest-neighbor method, which compares the distances between the unknown sample or instance and all the known instances in classification library 30. The class containing the instance with the shortest distance from the unknown instance is the closest match and may be chosen as the identity of the unknown instance. Many more sophisticated classification algorithms may also be used. Some of these algorithms may be used in conjunction with the nearest-neighbor method.

Produce recognition software 21 may automatically choose the identity of produce item 18 or display a short list of possible identifications for operator selection through a graphic user interface or other type of interface. For example, the operator may pick the correct identification by touching one of a number of color pictures of possible identifications on a touch-screen display. Transaction terminal 20 uses the identification information to obtain a unit price for produce item 18 from transaction server 24. Transaction terminal 20 then determines a total price by multiplying the unit price by weight information from scale 16 and, if necessary, by count information entered by the operator.

Operation returns to step 110 to await another signal from produce data collector 14.

Referring now to FIG. 6, the method of obtaining an internal reference calibration value (measured spectrum $F'_{ref}(\lambda)$) for step 112 in FIG. 5 begins with START 150.

In step 152, produce recognition software 21 closes shutter 102 thereby placing internal reference 62 in the light path.

step 154, produce recognition software 21 causes control circuitry 56 to activate light source 40. Light source 40 illuminates internal reference 62.

In step 156, produce recognition software 21 collects measured spectrum $F'_{ref}(\lambda)$ of internal reference 62 from control circuitry 56.

In step 158, produce recognition software 21 stores measured spectrum $F'_{ref}(\lambda)$ of internal reference 62 in calibration data 34.

In step 160, produce recognition software 21 opens shutter 102.

In step 162, operation ends.

Advantageously, the present invention facilitates inter-device calibration without operator involvement.

Although the invention has been described with particular reference to certain preferred embodiments thereof, variations and modifications of the present invention can be effected within the spirit and scope of the following claims.

We claim:

1. A produce recognition system comprising:
    a produce data collector for collecting first data from an external reference and second and third data from an internal reference, and for collecting fourth data from a produce item; and
    a computer coupled to the produce data collector which determines a first calibration value from the first and second data and a second calibration value from the third data, which applies the first and second calibration values to the fourth data to produce fifth data, which obtains sixth data from reference produce data, and which compares the fifth and sixth data to identify the produce item.

2. The produce recognition system as recited in claim 1, wherein the produce data collector comprises:
    a housing containing a window;
    a light source within the housing having a light path oriented through the window for illuminating the external reference and the produce item;
    a collector within the housing for collecting reflected light from the external reference, the internal reference, and the produce item; and
    a shutter assembly inside the housing for positioning the internal reference in the light path during collection of the second and third data.

3. The produce recognition system as recited in claim 2, wherein the collector is located in the housing at an opposite end of a reflected light path from the window, and wherein the shutter assembly also positions the internal reference in the reflected light path during collection of the second and third data.

4. The produce recognition system as recited in claim 1, wherein the produce data collector comprises:
    a memory for storing at least one of the first and second calibration values.

5. The produce recognition system as recited in claim 1, wherein the computer comprises a transaction terminal.

6. The produce recognition system as recited in claim 1, wherein the computer comprises a server.

7. A produce data collector comprising:
    a housing containing a window;

a light source within the housing having a light path oriented through the window;
  wherein the light source illuminates an external reference to obtain first data and an internal reference to obtain second data for use in determining a first calibration value;
  wherein the light source illuminates the internal reference to obtain third data for use in determining a second calibration value;
  wherein the light source illuminates a produce item to obtain fourth data to be calibrated by the first and second calibration values;
a collector within the housing for collecting reflected light from the external reference, the internal reference, and the produce item; and
a shutter assembly inside the housing for positioning the internal reference in the light path during collection of the second and third data.

8. The produce data collector as recited in claim 7, further comprising:
a memory for storing at least one of the first and second calibration values.

9. A produce recognition system comprising:
collecting means for collecting first data from an external reference and second and third data from an internal reference, and for collecting fourth data from a produce item; and
processing means coupled to the collecting means for determining a first calibration value from the first and second data and a second calibration value from the third data, for applying the first and second calibration values to the fourth data to produce fifth data, for obtaining sixth data from reference produce data, and for comparing the fifth and sixth data to identify the produce item.

10. A spectrometer comprising:

a housing containing a window;

a light source within the housing having a light path oriented through the window;
  wherein the light source illuminates an external reference to obtain first data and an internal reference to obtain second data for use in determining a first calibration value;
  wherein the light source illuminates the internal reference to obtain third data for use in determining a second calibration value;
  wherein the light source illuminates an object to obtain fourth data to be calibrated by the first and second calibration values;
a collector within the housing for collecting reflected light from the external reference, the internal reference, and the object; and
a shutter assembly inside the housing for positioning the internal reference in the light path during collection of the second and third data.

\* \* \* \* \*